(12) United States Patent
Jardine et al.

(10) Patent No.: US 11,517,381 B2
(45) Date of Patent: Dec. 6, 2022

(54) INTERCHANGEABLE INPUT HANDLES FOR A SURGEON CONSOLE OF A ROBOTIC SURGICAL SYSTEM

(71) Applicant: Asensus Surgical US, Inc., Durham, NC (US)

(72) Inventors: Nicholas J Jardine, Holly Springs, NC (US); Zachary S. Leonard, Raleigh, NC (US); Paul Wilhelm Schnur, Pipersville, PA (US)

(73) Assignee: Asensus Surgical US, Inc., Durham, NC (US)

( * ) Notice: Subject to any disclaimer, the term of this patent is extended or adjusted under 35 U.S.C. 154(b) by 267 days.

(21) Appl. No.: 16/732,945

(22) Filed: Jan. 2, 2020

(65) Prior Publication Data

US 2020/0205910 A1 Jul. 2, 2020

Related U.S. Application Data

(60) Provisional application No. 62/787,304, filed on Jan. 1, 2019.

(51) Int. Cl.
*A61B 34/30* (2016.01)
*A61B 34/00* (2016.01)

(52) U.S. Cl.
CPC .............. *A61B 34/30* (2016.02); *A61B 34/25* (2016.02); *A61B 34/70* (2016.02); *A61B 2034/742* (2016.02)

(58) Field of Classification Search
CPC ......... A61B 34/30; A61B 34/25; A61B 34/70; A61B 2034/742; A61B 34/37; A61B 34/74; A61B 34/76; A61B 2017/0046
See application file for complete search history.

(56) References Cited

U.S. PATENT DOCUMENTS

| | | | |
|---|---|---|---|
| 5,572,999 A * | 11/1996 | Funda | A61B 90/11 600/459 |
| 5,607,158 A * | 3/1997 | Chan | A63F 13/24 345/161 |
| 6,587,750 B2 | 7/2003 | Gerbi et al. | |
| 8,332,072 B1 | 12/2012 | Schaible et al. | |
| 8,377,044 B2 * | 2/2013 | Coe | A61B 17/00 606/1 |
| 8,638,057 B2 | 1/2014 | Goldberg et al. | |
| 8,753,296 B2 * | 6/2014 | Einav | A61H 1/0237 601/5 |
| 8,812,160 B2 | 8/2014 | Hagn et al. | |
| 8,930,027 B2 | 1/2015 | Schaible et al. | |
| 9,579,088 B2 * | 2/2017 | Farritor | A61B 17/00234 |
| 9,681,921 B2 * | 6/2017 | Gombert | A61B 34/32 |
| 9,696,700 B2 * | 7/2017 | Beira | G16H 40/67 |

(Continued)

OTHER PUBLICATIONS

Brooks T. L. et al., "Hand Controllers for Teleoperation" A State-of-the-Art Technology Survey and Evaluation. JPL Publication 85-11 (Mar. 1, 1985).

*Primary Examiner* — Julian W Woo

(57) ABSTRACT

A user interface for a surgical robotic system includes a plurality of handles, each removably attachable to a user interface assembly by a quick release connector. The selection of handles can include handles of varying size, degree of complexity, handles adapted for laparoscopic motion, handles adapted for true cartesian motion or handles customized to surgeon anthropometric data, etc.

9 Claims, 6 Drawing Sheets

(56) References Cited

U.S. PATENT DOCUMENTS

| | | |
|---|---|---|
| 9,763,739 B2 | 9/2017 | Schaible et al. |
| 9,827,059 B2 | 11/2017 | Robinson et al. |
| 10,251,716 B2 | 4/2019 | Overmyer |
| 10,921,904 B2 * | 2/2021 | Parazynski ............. G06F 3/014 |
| 2015/0223897 A1 | 8/2015 | Kostrzewski et al. |
| 2019/0201025 A1 * | 7/2019 | Shelton, IV ........... A61B 5/065 |

* cited by examiner

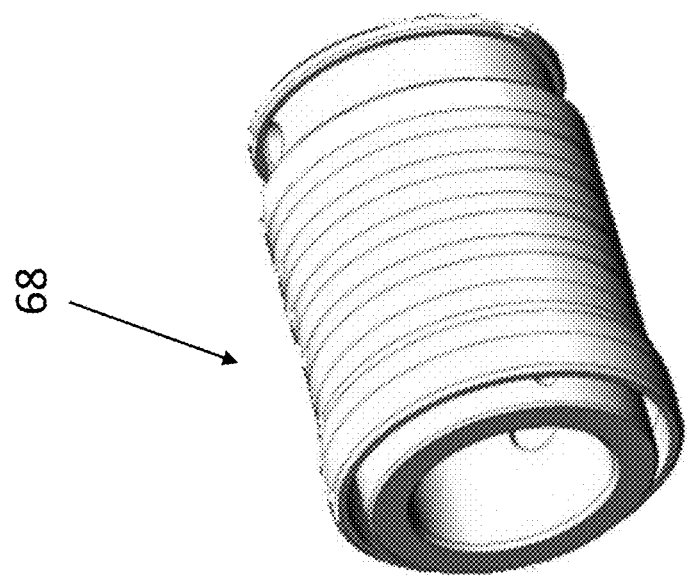
FIG. 6
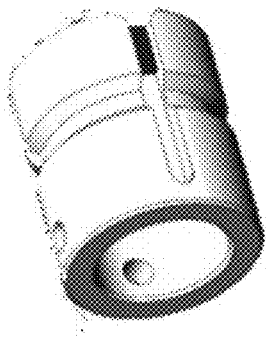
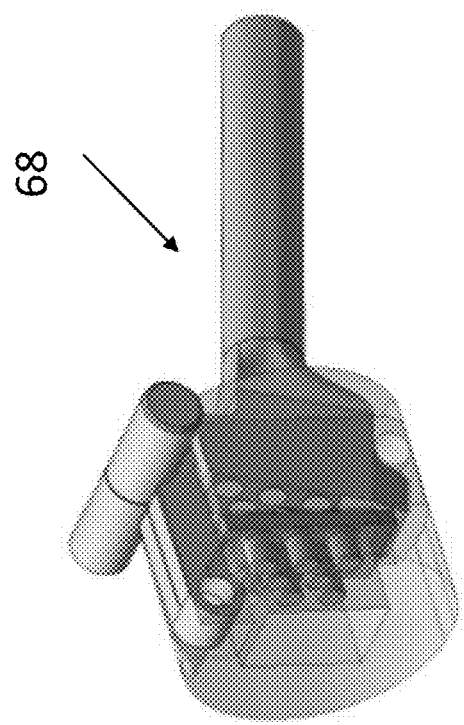
FIG. 5

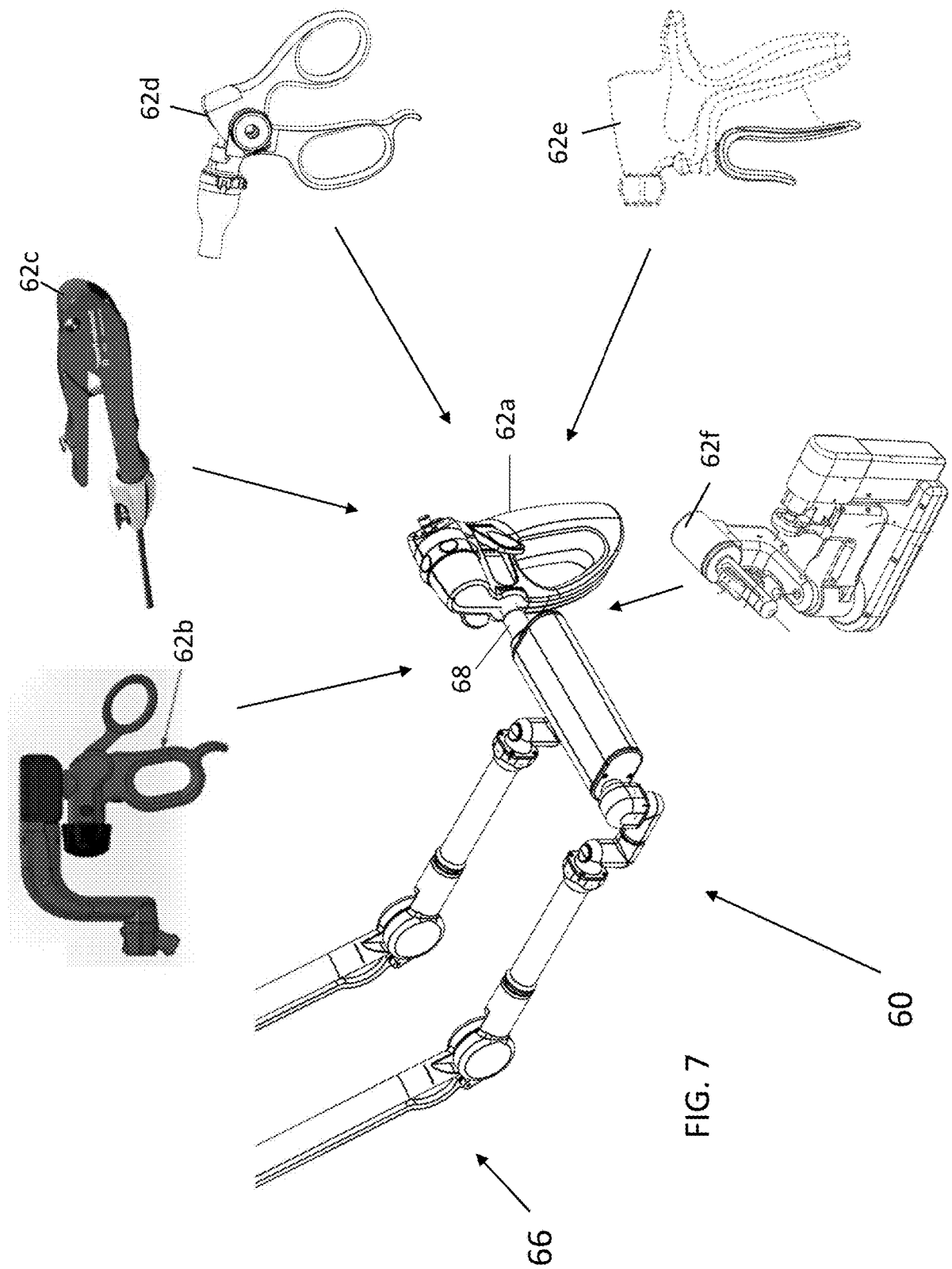

INTERCHANGEABLE INPUT HANDLES FOR A SURGEON CONSOLE OF A ROBOTIC SURGICAL SYSTEM

TECHNICAL FIELD OF THE INVENTION

The present invention relates generally to user input devices used to give input to robotic surgical systems for the control of robotically driven instrument. More particularly, the invention relates to handles usable for such systems.

BACKGROUND

Surgical robotic systems use one or more robotic manipulators or robotic arms. Each manipulator carries a surgical instrument, or the camera used to capture images from within the body for display on a monitor. Typical configurations allow two or three instruments and the camera to be supported and manipulated by the system. Input to the system is generated based on input from a surgeon positioned at a surgeon console, typically using input devices such as input handles and a foot pedal. Motion and actuation of the surgical instruments and the camera is controlled based on the user input. The image captured by the camera is shown on a display at the surgeon console. The console may be located patient-side, within the sterile field, or outside of the sterile field.

The console may include two input devices which can be gripped by the surgeon and moved so as to deliver instructions to the system as to the desired movement and operation of the instruments supported by the robotic arms. The surgeon's movements are suitably reproduced by the surgical instruments by means of movement of the robotic arms. The input devices may be equipped to provide the surgeon with tactile feedback so that the surgeon can feel on the input devices the forces exerted by the instruments on the patient's tissues.

Although the concepts described herein may be used on a variety of robotic surgical systems, one example of a system is shown in FIG. 1. In the illustrated system, a surgeon console 12 has two input devices such as handles 17, 18. The input devices 12 are configured to be manipulated by a user to generate signals that are used to command motion of a robotically controlled device in multiple degrees of freedom. In use, the user selectively assigns the two handles 17, 18 to two of the robotic manipulators 13, 14, 15, allowing surgeon control of two of the surgical instruments 10a, 10b, and 10c disposed at the working site (in a patient on patient bed 2) at any given time. To control a third one of the instruments disposed at the working site, one of the two handles 17, 18 may be operatively disengaged from one of the initial two instruments and then operatively paired with the third instrument, or another form of input may control the third instrument as described in the next paragraph.

One of the instruments 10a, 10b, 10c is a camera that captures images of the operative field in the body cavity. The camera may be moved by its corresponding robotic manipulator using input from a variety of types of input devices, including, without limitation, one of the handles 17, 18, additional controls on the console, a foot pedal, an eye tracker 21, voice controller, etc. The console may also include a display or monitor 23 configured to display the images captured by the camera, and for optionally displaying system information, patient information, etc.

A control unit 30 is operationally connected to the robotic arms and to the user interface. The control unit receives user input from the input devices corresponding to the desired movement of the surgical instruments, and the robotic arms are caused to manipulate the surgical instruments accordingly.

The input devices 17, 18 are configured to be manipulated by a user to generate signals that are processed by the system to generate instructions used to command motion of the manipulators in order to move the instruments in multiple degrees of freedom and to, as appropriate, control operation of electromechanical actuators/motors that drive motion and/or actuation of the instrument end effectors. As described in application US 2013/0012930, the ability to understand the forces that are being applied to the patient by the robotically controlled surgical devices during minimally invasive surgery is highly advantageous to the surgeon. Communication of information representing such forces to the surgeon via the surgeon interface is referred to as "haptic feedback." In some systems, haptic feedback is communicated to the surgeon in the form of forces applied by motors to the surgeon interface, so that as the surgeon moves the handles of the surgeon interface, s/he feels resistance against movement representing the direction and magnitude of forces experienced by the robotically controlled surgical device. Forces represented can include both the forces at the tips of the robotically controlled devices and/or the forces being applied by the shaft of the robotically controlled device to the trocar at the entrance point to the body, giving the surgeon complete understanding of the forces applied to the device so s/he can better control the device during surgery.

The surgical system allows the operating room staff to remove and replace the surgical instruments 10a, b, c carried by the robotic manipulator, based on the surgical need. When an instrument exchange is necessary, surgical personnel remove an instrument from a manipulator arm and replace it with another.

The number of degrees of freedom (DOFs) of motion for a robotically controlled instrument can vary between surgical systems and also between the different devices used for a particular system. Likewise, instruments with varying levels of complexity can be used interchangeably on a particular type of robotic system.

For example, a robotically controlled rigid-shafted instrument that moves similarly to a conventional laparoscopic instrument will be pivoted by the robotic arm relative to a fulcrum at the incision site (instrument pitch-yaw motion), axial roll of the instrument about its longitudinal axis, and translation along the longitudinal axis of the instrument (along the axis of insertion/withdrawal of the instrument relative to the incision). A user input device designed to give instruments for movement and actuation of this type of instrument can be fairly simple. For example, FIG. 2 shows a grip 50 that might be used on a user input device to move that type of simple robotically manipulated laparoscopic instrument. The grip 50 is very similar to a simple laparoscopic instrument grip, and it works with the remaining features of the user input device (linkages and/or gimbals, for example) so that the user directions movement of the surgical instrument using hand movements familiar to the laparoscopic surgeon. For example, the grip is pivoted in one direction to pivot the instrument tip in the opposite direction within the body, so that pivoting the instrument handle downwardly causes the robotic system to pivot the instrument tip upwardly, etc. The user advances/retracts the grip along its longitudinal axis to cause the robotic arm to advance/retract the instrument along its insertion axis. Pivoting one or two grip members 52 relative to the grip 50 is used as input to open/close the jaws of the instrument.

A robotically controlled rigid-shafted instrument that moves similarly to a conventional laparoscopic instrument having slightly more complexity than that described in the prior paragraph might require a slightly more complex grip for the user input devices. If, for example, the instrument adds a degree of articulation of its end effector about its shaft, and/or the ability to axially roll the instrument's tip about the shaft, a grip can be used to facilitate use of those features. In the example shown in FIG. 3, instrument pitch-yaw motion, instrument roll and insertion axis motion and jaw open-close can be achieved by moving the grip 54 in the same ways discussed with respect to the second embodiment. In addition, axial tip roll can be achieved by rotating a knob 56 or lever on the grip 54 (e.g. using the index finger), and movement of the degree of articulation can be commanded by pivoting the grip about pivot axis P.

Handles incorporating additional degrees of freedom might be needed for surgical instruments having greater complexity. For example, an instrument that includes an elongate rigid shaft having a region that can be robotically controlled to articulate or bend can have additional DOFs in the region of the articulation or bend. As a more specific example, such an instrument might be configured to move the instrument tip or end effector in pitch and/or yaw relative to the instrument shaft (i.e. in addition to the pitch and/or yaw that results from movement of the rigid instrument shaft about a fulcrum at the incision site), giving the instrument 6 DOFs. See, for example, the instruments described in co-pending and commonly owned application U.S. Ser. No. 16/732,306, Articulating Surgical Instrument.

There are other types of user instrument handle motion, besides laparoscopic motion, used in surgery. Another type of instrument handle motion used in surgery is referred to as "true cartesian motion," which differs from laparoscopic motion in that there is no inversion of the motion, so the user input handle is raised to cause the surgical robotic system to raise the instrument tip, moved left to cause movement of the tip to the left, etc. Some surgical systems may allow surgical personnel to choose whether the system will operate in a laparoscopic type of mode or in a true cartesian motion mode. Others might make use of a surgeon console that is configured so it can be selectively used use with a laparoscopic surgical system and with a true cartesian surgical system.

Surgeons may have functional or ergonomic preferences concerning the style, set-up or functionality of the handles of the input devices. Surgeons with larger hands might choose larger handles while surgeons with smaller hands might choose smaller handles. Surgeons might also have preferences as to the type of grip members that are used to direct jaw open-close handles, and the type of knobs or other input mechanisms used to direct instrument tip roll. A surgeon might also have a preference as to whether s/he wishes to give input using (a) laparoscopic type of motion, or (b) true cartesian motion. Moreover, as discussed, some surgical instruments have multiple degrees of freedom, requiring input devices that can give input to control those degrees of freedom. Other instruments that are more akin to traditional "straight stick" laparoscopic instruments lack degrees of freedom beyond pitch and yaw motion relative to the incision site, and motion along the instrument's insertion axis. Input for this latter type of instrument can thus be given using a relatively simple form of user input device.

This application describes input devices for robotic-assisted surgical systems that allow easy replacement of grips/handles in order to suit surgeon preferences.

BRIEF DESCRIPTION OF THE DRAWINGS

FIG. 5 shows a latch lock type of connection for an interchangeable handle interface;

FIG. 6 shows a twist lock type of configuration for an interchangeable handle interface;

FIG. 7 illustrates a user interface device and a collection of interchangeable handles.

DETAILED DESCRIPTION

Figure 1:
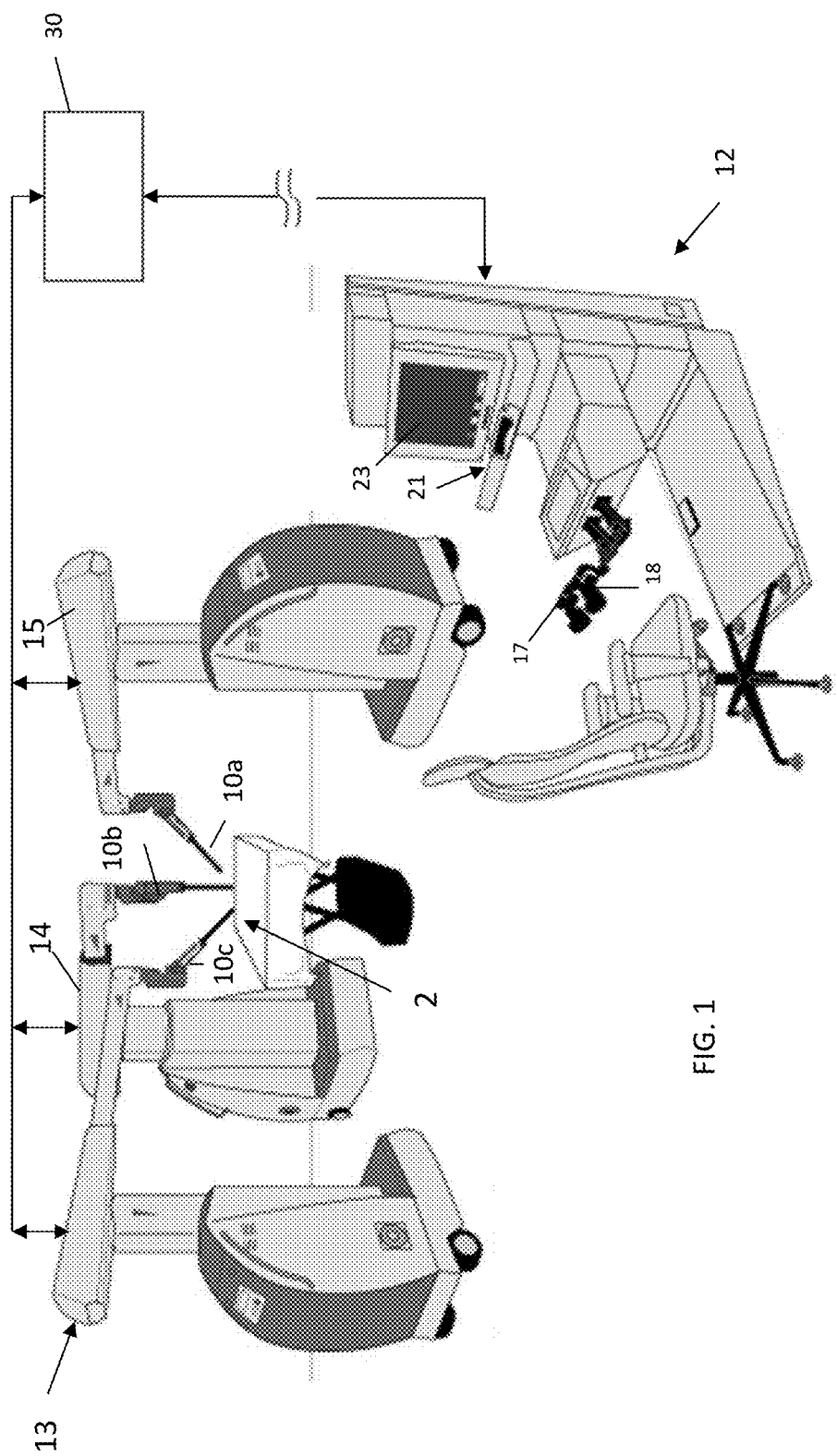
FIG. 1 is a perspective view of an example of a robot-assisted surgical system having a surgeon console of a type with which the configurations described herein may be use.
Figure 3:
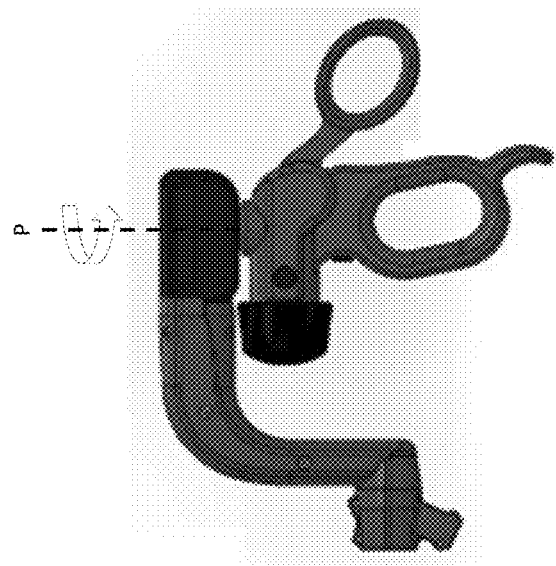
FIG. 3 is a side view of a second example of a grip for a user input device.
Figure 2:
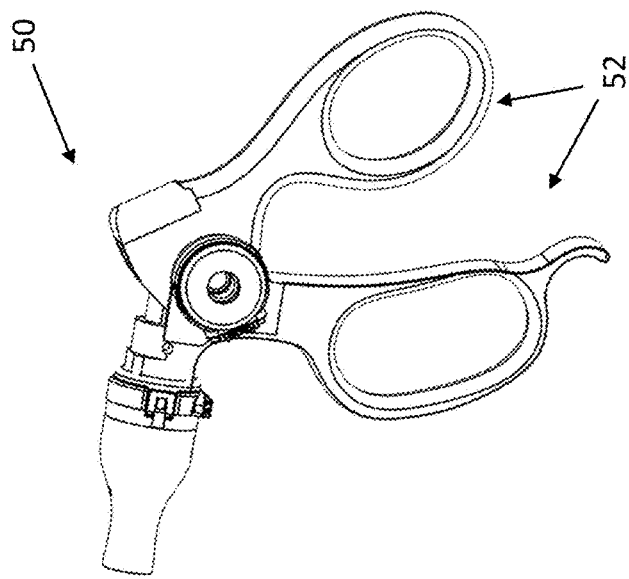
FIG. 2 is a side view of a first example of a grip for a user input device.

The purpose of the disclosed invention is to provide a user interface device 60 configured to allow surgical staff to customize a user interface or a surgical robotic system to the specific instrument and/or user preference. The user interface device 60 is preferably part of a surgeon console for a robotic surgical system (see, for example, surgeon console 12 of FIG. 1). The concepts described here are suitable for use with any type of user interface device 60 that is manipulated by a user to generated input to a surgical robotic system for manipulation of a corresponding surgical instrument. Examples include the user interface of the surgeon console of the Senhance Surgical System marketed by TransEnterix, Inc., Morrisville, N.C., a user interface device of the type described in co-pending and commonly owned U.S. application Ser. No. 16/513,670 ("Haptic User Interface for Robotically Controlled Surgical Instruments") and any other type of interface.

Figure 4:
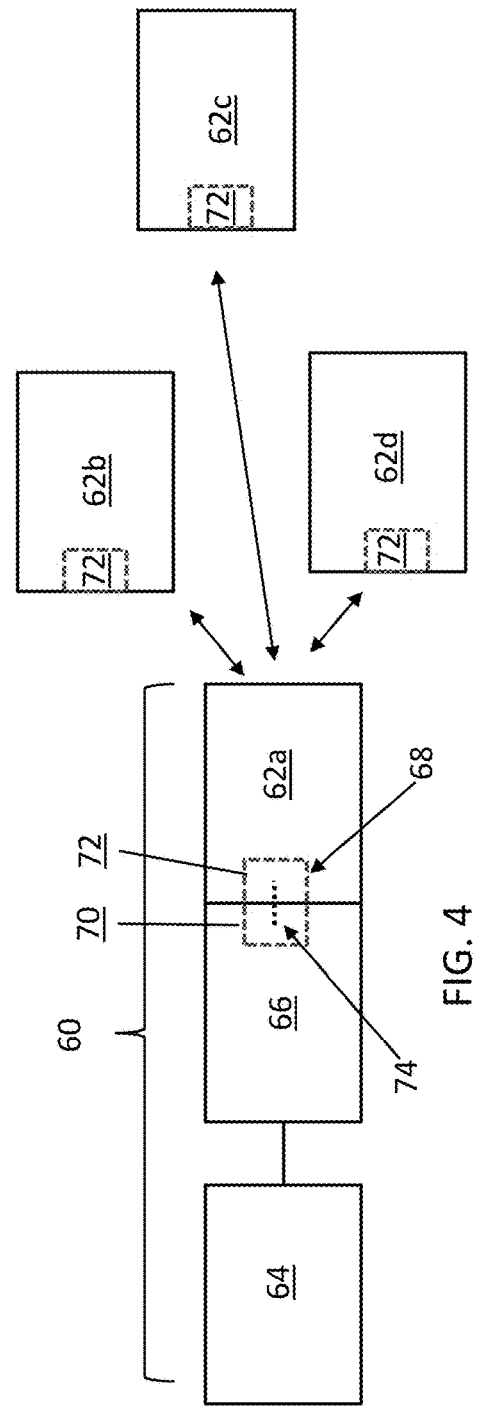
FIG. 4 schematically depicts a user interface device having interchangeable handles.

FIG. 4 schematically depicts a user interface device 60. User interface device 60 has a handle 62 that a user manipulates to generate input to a surgical robotic system to cause movement of a corresponding surgical instrument within the patient's body. A base 64 that remains stationary during use is coupled by an interface assembly 66 (e.g. linkages, and/or gimbals, sliding interfaces, and/or other structures that permit movement of the handle relative to the base). The interface assembly includes sensors (not shown) such as encoders or the like convert motion of components of the interface assembly resulting from movement of the handle into signals used to control movement of the corresponding surgical instrument. A connector 68 releasably connects one of a plurality of interchangeable handles 62a-62d to the interface assembly 66. Connector includes a first part 70 on the interface assembly 66 and a second part 72 on the removable handle. The connector 68 is preferably a quick-release connector, defined herein to mean any type of connector whose parts may be securely engaged/disengaged without use of a separate tool. Examples include twist locks, straight insertion locks (FIG. 6), latch locks (FIG. 5), any of a variety of quick release couplings used to connect two comments (including, without limitation, ones similar to types used to connect fluid lines in medical and industrial fields). The connectors 68 may include poka-yoke features to ensure the handles are installed in the proper orientation and, where there are left- and right-handed versions for a two-interface surgeon console, on the correct side of the console.

FIG. 7 illustrates one example of a user interface device 60 in which the interface assembly 66 (a portion of which is shown) is the type described in co-pending U.S. application Ser. No. 16/513,670 ("Haptic User Interface for Robotically Controlled Surgical Instruments") and in which various non-limiting examples of handles 62a-f are shown.

Figure 8B:
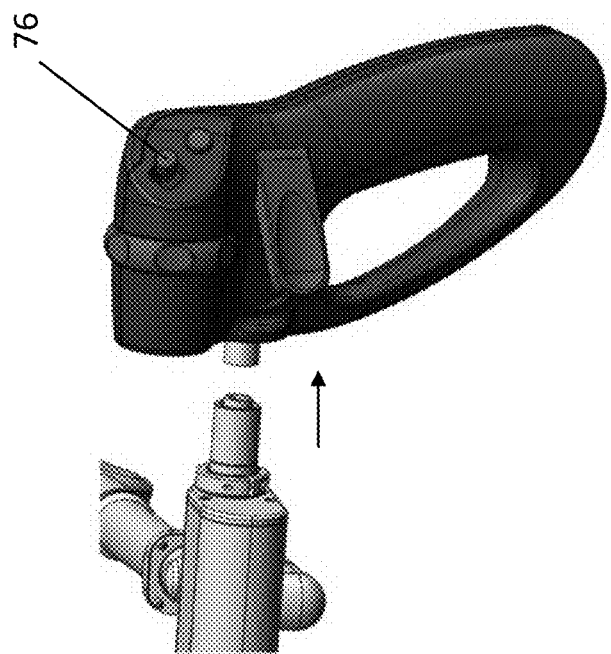
FIGS. 8A and 8B illustrate detachment of an exemplary interchangeable handle from a user interface device.

In use, the quick release connector is released and the handle that is on the interface assembly is withdrawn from the interface assembly as indicated in FIG. 8B. A replacement handle is then mounted to the interface assembly using the quick release connector.

The selection of handles 62a-f can include handles of varying degree of complexity, handles of different sizes and/or shapes, handles adapted for laparoscopic motion, handles adapted for true cartesian motion 62f, handles having different grip configurations (e.g. scissor grip, pistol grip, etc.) or jaw actuation mechanisms (e.g. scissor handle type arrangements, two- or one-lever mechanisms, triggers, finger loops, paddle arrangements (described in connection with FIG. 9), and/or handles customized to surgeon anthropometric data. Examples of the handle types described above in the Background may be included.

Some handles may incorporate tactile (e.g. vibratory) motors and/or brushed/brushless DC motors for haptic feedback. Some, as with the embodiment shown in FIGS. 8A-9, can incorporate mechanical or optical joystick control features 76. In one configuration in which a surgical instrument having pitch and jaw articulation at its distal end (e.g. one of the type described in U.S. Ser. No. 16/732,306, entitled Articulating Surgical Instrument), movement of the handle itself will control instrument yaw and pitch motion etc., while the joystick will be moved by the user (e.g. thumb control) to cause pitch/yaw articulating at the end effector). In other embodiments, the joystick is used to control movement of another surgical instrument, such as the camera that is positioned on the body. This may control laparoscopic movement of the camera (as moved by the robotic arm supporting it), or articulation/bending at the distal end of the instrument. Other uses for the joystick include menu selection functions.

Figure 8A:
Figure 10:
FIG. 10 shows the handle of FIG. 8A with the paddles separated from the handle.
Figure 9:
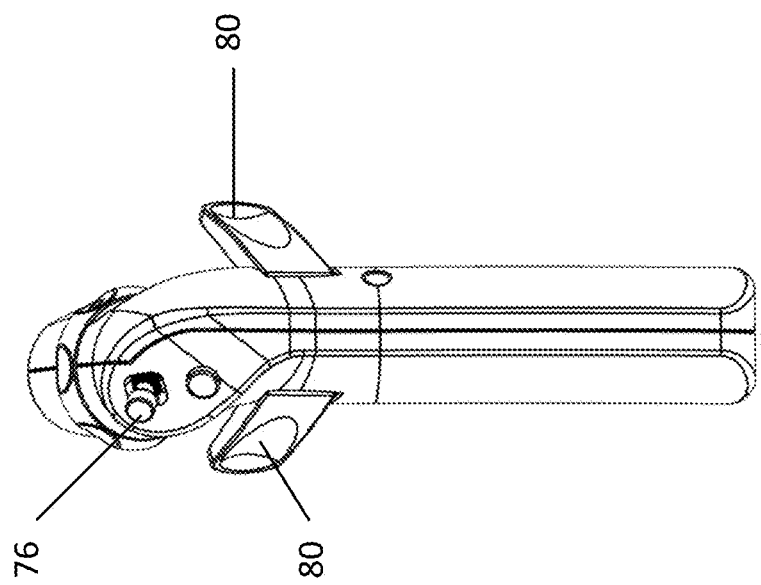
FIG. 9 is a rear view of the handle of FIG. 8A.

The FIG. 8A-9 handle 62a further includes paddle members 80 for jaw open/close functions. Note that in alternative handles only one of the paddle members 80 might be used. As illustrated in FIG. 10, the interchangeable handles 62a might include interchangeable features on them, allowing components of the handle itself to be modified according to the intended surgical task, anthropometrics, surgeon preference, human factors, etc. In this example, the paddles 80 of the interchangeable handle may be replaced with alternative paddles 80a that have different properties such as different size, shape, contact surface contour, open/close ranges etc. In other embodiments, triggers, finger loops, joystick members or other components can be interchangeable.

Handles might also include additional buttons, switches and/or toggles to provide additional forms of input to the surgical system used to control various other features, including clutching (suspension of the control relationship between handle motion and instrument), application of energy by the surgical instrument, and/or enabling/disabling certain features of the surgical robotic system. For example, a switch may be used to instruct the system to turn on eye-tracking camera control of the type described in commonly owned U.S. patent Ser. No. 10/251,713).

In some cases, the interchangeable handles may be provided as sterile, sterilizable, or disposable, options which would allow the surgeon to operate the interface while scrubbed in in the surgical field. In sterile embodiments, the handle may be placed under a sterile drape. In a sterilizable embodiment, the handle is designed to withstand cleaning and sterilization processes. Disposable embodiments are designed as single-use, disposable components.

In some configurations, mechanical and/or electrical/electronic controls 74 (FIG. 4) may be routed through the connector 68. This can allow sensitive motors and electronics used for functions of the handle (e.g. joystick operation, vibrational or jaw activation haptics, switch operation) to reside in the interface assembly rather than in the handle, reducing the cost of the handles and allowing the handles to be disposable. Mechanical controls 74 can include rods, cables, shafts, linkages and the like.

It may also be advantageous to transmit data and power between the handle and the surgeon console without contacts. Methods of contactless power and data transmission are described in U.S. application Ser. No. 16/051,466 ("Contactless Power and Data Transmission for Surgical Robotic System") and U.S. application Ser. No. 16/732,935, filed on the same day as the present application ("Optical Data Transmission in a Wireless Power Transmitter for a Surgical Robotic System")(Attorney Ref: TRX-14700R).

In a handle configuration with a brushless DC motor, hall sensor, encoders, or other IO, there can be upwards of 20 signals transmitted between the handle and the interface assembly. Directly transmitting large numbers of signals such as these would require a large connector that may be unrealistic for a user mechanism of the desired size. The connector and associated wire harness would add weight to the mechanism and decrease its reliability. An embodiment therefore includes a PCBA that serializes the various signals communicated through the handle to reduce the number of signals transmitted between the handles and the console. In this embodiment, there would be an associated PCBA to deserialize the handle signal to extract the individual signals. One embodiment for a serialized communication scheme with a representative handle configuration could implement power and data transmission through the connector 68 in 8 pins: 3 pins for the motor winding, and pins for each of serializer power, serializer ground, serializer signal A, serializer signal B, and an earth ground.

Another embodiment for power transfer to the handle includes incorporating battery power into the handle. The battery could be designed for a single-use, disposable handle, could be designed with capacity for a finite use life, or it could be rechargeable between procedures using either contacts or wireless charging (e.g. Qi, PMA or proprietary standard). Incorporating a battery into the handle is another method to reduce the number of contacts at the handle interface and to enable improved design for sterility/sterilization.

All patents and patent applications referenced herein, including for purposes of priority, are incorporated herein by reference.

We claim:

1. A user interface for a surgical robotic system, comprising:
 a base;
 an interface assembly connected to the base and moveable relative to the base to generate signals for use by a surgical robotic system to control motion of a surgical instrument;

a plurality of handles, each removably attachable to the interface assembly by a quick release connector, wherein a first one of the plurality of handles includes a handle body moveable relative to the base, and a joystick on the handle body, the joystick moveable with respect to the handle body;

wherein the user interface is operable to cause movement of a first surgical instrument having an elongate shaft with an articulating distal portion, wherein the handle body of the first one of the plurality of handles is moveable relative to the base to cause the robotic system to move the first instrument shaft relative to an incision through which the first instrument extends, and wherein the joystick is moveable relative to the handle body to cause articulation of the articulating distal portion relative to the shaft.

2. The user interface according to claim 1, wherein the quick release connector has an engaged position in which the handle is fixed to the interface assembly, and a disengaged position in which the handle is removable from the interface assembly, wherein the quick release connector is connector moveable between the locked position and the unlocked position without use of a separate tool to allow attachment and detachment of the corresponding handle from the interface assembly.

3. The user interface according to claim 2, wherein the quick release connector is a twist lock.

4. The user interface according to claim 2, wherein the quick release connector is a straight insertion lock.

5. The user interface according to claim 2, wherein the quick release connector is a latch lock.

6. The user interface according to claim 1, wherein a first one of the plurality of handles is customized to surgeon anthropometric data.

7. The user interface according to claim 1, wherein the user interface is further operable to cause movement of second and third surgical instruments, wherein the handle body of the first one of the plurality of handles is moveable relative to the body to cause the robotic system to move the third instrument, and wherein the joystick is operable to cause movement of the second surgical instrument.

8. The user interface according to claim 1, wherein a first one of the plurality of handles includes electronic components, and wherein the quick release connector is configured to wirelessly transmit power between the user interface and the electronic components.

9. The user interface according to claim 1, wherein at least one of the plurality of handles includes an input for initiating delivery of energy to tissue by a surgical instrument.

* * * * *